(12) United States Patent
Mizutani et al.

(10) Patent No.: US 7,329,243 B2
(45) Date of Patent: Feb. 12, 2008

(54) INTER-LABIAL PAD

(75) Inventors: Satoshi Mizutani, Kagawa (JP); Wataru Yoshimasa, Kagawa (JP); Yuki Noda, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 11/142,008

(22) Filed: May 31, 2005

(65) Prior Publication Data
US 2005/0273069 A1    Dec. 8, 2005

(30) Foreign Application Priority Data
May 28, 2004    (JP) .............................. 2004-160162

(51) Int. Cl.
*A61F 13/15*    (2006.01)

(52) U.S. Cl. ............ 604/385.01; 604/358; 604/385.17; 604/385.201

(58) Field of Classification Search ......... 604/385.201, 604/385.17, 385.01, 358
See application file for complete search history.

(56) References Cited

U.S. PATENT DOCUMENTS

| | | | | |
|---|---|---|---|---|
| 4,595,392 A | * | 6/1986 | Johnson et al. | ........ 604/385.17 |
| 4,631,062 A | | 12/1986 | Lassen et al. | |
| 4,673,403 A | * | 6/1987 | Lassen et al. | ........... 604/385.17 |
| 4,846,824 A | * | 7/1989 | Lassen et al. | ........... 604/385.17 |
| 5,672,165 A | * | 9/1997 | Belecky et al. | ............. 604/383 |
| D404,814 S | * | 1/1999 | Mayer | ........................ D24/125 |
| 6,932,801 B1 | * | 8/2005 | Samuelsson | ........... 604/385.17 |

2002/0193770 A1    12/2002    Edens et al.

FOREIGN PATENT DOCUMENTS

| | | |
|---|---|---|
| EP | 0 162 451 B1 | 8/1991 |
| EP | 1 407 745 A1 | 11/2002 |
| EP | 1 407 739 A1 | 4/2004 |
| EP | 1407737 A1 * | 4/2004 |
| EP | 1407742 A1 * | 4/2004 |
| JP | 7-18712 U | 4/1995 |
| JP | 2002-513638 A | 5/2002 |
| JP | 2003-038562 A | 2/2003 |
| JP | 2004-024821 A | 1/2004 |
| JP | 2004-097693 A | 4/2004 |
| JP | 2004-121611 A | 4/2004 |
| JP | 2004-141620 A | 5/2004 |
| JP | 2004-141626 A | 5/2004 |
| JP | 2004-141627 A | 5/2004 |

(Continued)

*Primary Examiner*—Tatyana Zalukaeva
*Assistant Examiner*—Ginger Chapman
(74) *Attorney, Agent, or Firm*—Darby & Darby P.C.

(57) ABSTRACT

An inter-labial pad which can be inserted easily to a point of insertion is provided. An inter-labial pad 1 having an absorbent body for absorbing a body fluid is covered with a cover sheet, wherein a top portion 10 to be in contact with the depth of labia when the inter-labial pad 1 is put between the labia is provided. The top portion 10 has a shape different between the forward end 10a coming in contact with the forward of the labia and the backward end 10b coming in contact with the backward of the labia upon attachment, with the backward end being in a sharp shape and of narrow width and sharp angle. Thus, the inter-labial pad 1 can be inserted easily from a sharp backward end 10b easily to the labia.

11 Claims, 8 Drawing Sheets

FOREIGN PATENT DOCUMENTS

| | | |
|---|---|---|
| JP | 2004-141628 A | 5/2004 |
| JP | 2004-141629 A | 5/2004 |
| WO | WO-02/094150 A1 | 11/2002 |
| WO | WO-02/094162 A1 | 11/2002 |
| WO | WO-02/100312 A2 | 12/2002 |

* cited by examiner

INTER-LABIAL PAD

CROSS-REFERENCE TO RELATED APPLICATIONS

This application is based upon and claims the benefit of priority from Japanese Patent application No. 2004-160162 filed on May 28, 2004, the entire contents of which is incorporated herein by reference.

FIELD OF THE INVENTION

The present invention relates to a sanitary article in which an absorbent body that absorbs a body fluid is covered with a cover sheet and, specifically, an inter-labial pad which is used being inserted between labia and, more in particular, it relates to the an inter-labial pad easily attached to the labia.

RELATED ART

Sanitary napkins and tampons have been used generally as female sanitary articles. For the sanitary napkins, a great effort has been made in order to prevent leakage of menstrual blood from a gap caused by insufficient adhesion to the vicinity of ostium vaginae. Further, also for the tampons, since they cause foreign-body sensation, uncomfortable feeling upon wearing and difficulty in inserting to the inside of a vagina, various devices have been made in order to avoid them.

Under these circumstances, sanitary articles referred to as inter-labial pads, which are a hybrid type merging the features of the sanitary napkins and the tampons, have become noted in recent years. The inter-labial pad is partially inserted between female labia so as to be abutted against the inner surface of the labia. Accordingly, since the inter-labial pad has a highly close adherence to a body compared to the sanitary napkin, leakage of the menstrual blood as well as the broad contact of diffused menstrual blood with the body can be prevented so that it is sanitary and clean. Further, since the inter-labial pad is smaller in the size compared to the sanitary article, the inter-labial pad has a feature that it is excellent in the feeling of wearing and comfortable, and causes less psychological resistance compared to the tampon to be inserted inside of the vagina.

However, since the inter-labial pad is to be inserted between the labia which are difficult to see, it has a drawback that inserting is more difficult than the sanitary napkin. Moreover, in a case where the inter-labial pad is not inserted in the appropriate position, damage due to leakage will be greater because it is smaller than the sanitary napkin in size. Further, a possibility of the erroneous inserting thereof is higher than that of tampons.

A device that tends to improve the difficulty in inserting the inter-labial pad is disclosed in the patent document 1. This patent document discloses an inter-labial pad comprising a liquid permeable surface side sheet that allows a body fluid to permeate therethrough, a less liquid permeable back face sheet that does not substantially allow the body fluid to permeate therethrough, and an absorbent body enclosed between these sheets. In this inter-labial pad, the surface covered with the surface side sheet becomes a body-contacting face, and the back face sheet covering the surface opposite to the surface side sheet is provided with a grip tab constituted with a semi-spherical protrusion. The grip tab is provided for inserting the inter-labial pad to the between labia. According to this inter-labial pad, since a wearer can insert the inter-labial pad by pinching the grip tab with fingers, it is considered that the pad can be inserted more easily than in a case with no grip tab.

However, it is difficult to abut the inter-labial pad so that it is sufficiently in close contact in the labia by merely pinching the grip tab. Further, with the structure described above, when the pad is intended to be inserted by pinching the grip tab with fingers, since the inter-labial space is extremely so narrow, that it is difficult to insert a portion for the thickness of fingers in the labia and, if the inter-labial pad is inserted forcibly, the inter-labial pad is inserted in a deformed state. Therefore, a gap may be formed between the labial inner wall and the inter-labial pad so as to induce the menstrual blood leakage and the inter-labial pad may be detached from the labia.

Further, in the inter-labial pad disclosed in the patent document described above, since the inserting point is sought with tips of wearer's fingers, it has to be inserted relying on the wearer's feeling in the actual case and it is not easy for the wearer to recognize an appropriate point for attachment. Particularly, in a case where the wearer has long nails or fake tips, it is extremely difficult to insert the conventional inter-labial pad described above in position.

As described above, the inter-labial pad disclosed in the patent document has not yet been enabling the facilitation for inserting, the decrease in erroneous inserting or the sufficiently close adhesion to a pubic region by appropriate recognition for the point of inserting Further, adherence of the menstrual blood to finger tips, etc., may still occur upon inserting, which is a part of the reasons causing feeling of resistance in the use of the inter-labial pad.

[Patent literature 1] International Patent Application laid-open No. WO99/56689 pamphlet

SUMMARY OF THE INVENTION

As has been described above, it was difficult for the conventional inter-labial pad to prevent injury for the inside of the labia and easily find a point of inserting. In view of the problems, the present inventors have noted that since the labia are in such a shape that they are longer and thicker at the forward portion while shorter and thinner at the backward portion, the backward portion of the labia are easy to open, and have accomplished the present invention.

The present invention has been achieved in view of the problems described above and intends to provide an inter-labial pad that can prevent injuries in the labia and can be inserted easily. Specifically, the invention intends to provide an inter-labial pad that can be inserted easily in position by starting intrude it from the backward of the labia and inserting the pad between the labia.

The present invention provides the following.

(1) An inter-labial pad which is used being inserted between labia, comprising a pair of side portions to be in contact with a pair of opposed inter-labial inner walls in the inserted state and a top portion to be in contact with the depth of the labia in the inserted state, wherein the top portion has a forward end to be in contact with the forward of the labia and a backward end situated opposite to the forward end, and at least the backward end has a sharp shape.

According to the present invention, the inter-labial pad comprises the top portion which is to be in contact with the depth of the labia. The top portion comprises the forward end to be in contact with the forward of the labia situating on the ventral side and the backward end situating opposite to the forward end and in contact with the backward of the labia situating on the dorsal side. In the present invention, at least the backward end has a sharp shape with a narrow width. "Sharp shape" means that the width is narrower and the shape of the backward end is relatively made sharper compared to the shape of the forward end.

This facilitates the intrusion of the inter-labial pad to the labia at the backward thereof so as to enable to insert the inter-labial pad while opening the inter-labial space from the backward to the forward of the labia. Accordingly, when the inter-labial pad is inserted between the labia, it is unnecessary to exert an excessive force of fingers and can prevent the deformation of the inter-labial pad thereby preventing formation of the gap between the inter-labial inner wall and the inter-labial pad. Further, the inter-labial pad can be thus easily inserted to the attaching position and this can avoid the risk of injuring the inside of the labia upon insertion of the inter-labial pad.

The inter-labial pad may be of any optional shape so long as it can be held between the female labia and, for example, it may be a flat plate shape in which a substantially plate-like absorbent body is covered with a cover sheet as described below in (4), or it may be a pillow-like shape in which a thick absorbent body is covered with a cover sheet. The plate-like inter-labial pad is folded in two substantially along the longitudinal center and inserted between the labia from the fold and then attached in a state where the portions of the absorbent body situated on both sides of the fold are in contact with the labial inner wall. In the case of the plate-like inter-labial pad, the top portion is formed along the fold, and the portions of the absorbent body situated on both sides of the top portion and in contact with the labial inner walls constitute the side portions.

On the other hand, in the pillow-like inter-labial pad, a pair of substantially plate-like opposed surfaces constitute the side portions in contact with the labial inner wall, a top portion is formed along the side edge connecting the end edges of the side portions to each other, and the pillbw-like inter-labial pad is inserted from the top portion to the depth of the labia.

(2) The inter-labial pad as described in (1) wherein the angle at the backward end of the top portion is smaller than the angle at the forward end of the top portion.

According to this embodiment of the present invention, the backward end of the top portion of the inter-labial pad has a smaller angle than that of the forward end and is pointed. That is, the forward end has a more moderate shape than the backward end. Accordingly, the inter-labial pad can be inserted between the labia easily from the pointed backward end.

(3) The inter-labial pad as described in (2), wherein the angle at the backward end of the top portion is from 2° to 45°, and the angle at the forward end of the top portion is from 30° to 150°.

According to this embodiment of the present invention, the angle of the top portion formed into a sharp shape is from 2 to 45° for the backward end and from 30 to 150° for the forward end. In a case where the angle of the top portion is within this range, insertion of the inter-labial pad between the labia is facilitated, and this can retain a shape with which the inter-labial pad is reliably held between the labia.

(4) The inter-labial pad as described in any one of (1) to (3), wherein the inter-labial pad comprises a substantially flat plate-like absorbent body that absorbs a body fluid, a surface side sheet covering one surface of the absorbent body to be in contact with a body in the inserted state and a back face sheet covering the other surface of the absorbent body, wherein the top portion is formed by folding the inter-labial pad in two such that the resulting pair of side portions of the back face sheet oppose to each other, and wherein the backward end of the top portion is formed into a sharp shape by adhering the pair of side portions of the back face sheet to each other.

According to this embodiment of the present invention, the substantially plate-like absorbent body is covered with the cover sheet. Such an inter-labial pad is folded in two along a line substantially passing the lateral center and in parallel with the longitudinal direction (hereinafter referred to as "longitudinal center line") and attached between the labia. The inter-labial pad comprises the liquid permeable surface side sheet in which the cover sheet allows a body fluid to permeate therethrough and a less liquid permeable back face sheet that does not substantially allow the body fluid to permeate therethrough and is attached with the surface side sheet being in contact with the depth of the labia and the labial inner wall. That is, the inter-labial pad according to the present invention is folded along the longitudinal center line and used in a state where the surface side sheet becomes the outer side and the back face sheet becomes the inner side. Since the folded inter-labial pad has the top portion along the fold and a pair of side portions of the back face sheet situating at the backward end of the top portion are adhered to each other, the part of the top portion is formed as a sharp shape.

As described above, since the pair of the side portions of the back face sheet are adhered to each other so as to be releasable and the top portion is formed into a sharp shape at the backward end, the inter-labial pad can be intruded easily between the labia in a case of inserting the inter-labial pad into the labia.

A sheet piece (hereinafter referred to as "mini-sheet") may be disposed on one surface of the back face sheet at the surface opposite to the side in contact with the absorbent body to form a pocket for insertion of a finger. The mini-sheet piece can be formed such that it covers a portion of the back face sheet, one side edge thereof opens to form an inlet of the pocket and with the other side edge being adhered to the back face sheet.

(5) The inter-labial pad as described in (4), wherein the pair of side portions of the back face sheet are adhered to each other so as to be releasable by a pressure caused by a movement of a wearer.

According to this embodiment of the present invention, the inter-labial pad is formed such that the adhered side portions of the back face sheet are released from each other by the exerting a wearing pressure to the inter-labial pad after insertion. In a case where pair of side portions of the back face sheets are releasably adhered as described above, the inter-labial pad can easily be intruded between the labia when the inter-labial pad is attached between the labia and, since the pair of side portions of the back face sheet are released from each other to eliminate the sharp shape when the pressure exerts on the inter-labial pad by the change of the wearer's posture after insertion, it hardly gives a foreign-body sensation to a wearer.

Means for adhering the side portions of the back face sheet releasably from each other includes adhesive coating, heat sealing and engaging fabrication.

Adhesives for adhering releasably the side portions of the back face sheet to each other include, for example, pressure sensitive adhesives mainly comprising rubbers or olefinic materials and heat sensitive adhesives. The rubber materials include, for example, styrene-ethylene-butylene-styrene block copolymer (SEBS), styrene-butadiene-styrene block copolymer (SBS), and styrene-isoprene-styrene block copolymer (SIS). Further, the olefinic materials include linear low density polyethylene, etc. Among them, the heat sensitive adhesives are particularly preferred because side portions of the back face sheet released by a body pressure are not adhered to each other even when they are in contact again with each other. Specific examples include those adhesives formed by melting and mixing from 5 to 25% of SEBS, from 40 to 60% of saturated alicyclic hydrocarbons, from 1 to 10% of modified aromatic terpenes, and from 15 to 35% of additives.

Further, those adhesives coming off by not only the body pressure but also being moistened by absorption of a body fluid, etc. may also be used. Adhesives that change the adhesiveness depending on moisture include water sensitive adhesives. Specifically, they include, for example, polyvinyl alcohol, carboxymethyl cellulose or gelatin as water soluble polymers, or polyvinyl acetate and sodium polyacrylate as water swellable polymers.

The coating position of the adhesives is not particularly limited so long as they are coated to the back face sheet on the side of the backward end. Further, in a case where the backward end formed into the sharp shape comprises a surface side sheet and a back face sheet enclosing no absorbent body between them, that is, when it comprises merely a surface side sheet and a back face sheet, the coating position is preferably disposed so as to be put between the surface side sheet and the back face sheet.

Further, the coating position may also be between a pair of opposed side portions of the back face sheet folded in two. By coating the adhesives also between the pair of side portions of the back face sheet, the adhesives can be reliably coated to the backward end to adhere the side portions of the back face sheet at the backward end to each other even in a case of adopting summit gun coating with fine coating pitch for the adhesives. Further, for adhering the side portions of the back face sheet to each other so as to be come off when required, it is preferred to extremely decrease the coating amount and the coating area of the adhesives. In a case where the coating amount of the adhesives, etc. is decreased, the amount of the adhesives exuded between the surface side sheet and the back face sheet upon cutting operation is also decreased. However, the side portions of the back face sheet can be adhered reliably to each other by coating the adhesives between each of the respective opposed side portions of the back face sheet.

The adhesive coating pattern includes, for example, spiral coating, controlled seam coating, coater coating, curtain coater coating and summit gun coating, etc. Among them, the summit gun coating is preferred since the pitch between the joined portion and the not-jointed portion can be made finer. A basis weight per unit area of the adhesives is within a range from 1 to 30 g/m$^2$ and, preferably, within a range from 3 to 10 g/m$^2$. In this case, the basis weight per unit area at the backward end may be made larger than that in other regions so as to facilitate the heat sealing. Further, when the adhesive is coated in a linear pattern, the line width is preferably within a range from 30 to 300 μm. In a case where the surface side sheet comprises a fiber assembly, when the basis weight per unit area thereof is less than 1 g/m$^2$ or the line width is less than 30 μm, the adhesives coated between the surface side sheet and the back face sheet are buried between the fibers of the surface side sheet failing to obtain a sufficient adhesion strength. On the other hand, in a case when the basis weight is more than 30 g/m$^2$ or the line width is more than 300 μm, the peripheral edge coated with the adhesives is stiffened. The coating pattern for the adhesives described above is applicable not only to the case of adhering the surface side sheet and the back face sheet but preferably also to a case of adhering the side portions of the back face sheet to each other.

(6) The inter-labial pad as described in (5) wherein the pair of side portions of the back face sheet is adhered by application of heat sealing or engaging fabrication so as to be released when necessary. According to this embodiment of the present invention, since a sharp shape can be constituted without interposing a constituent member such as adhesives between each of the opposed side portions of the back face sheet, the sharp shape can be formed easily in appropriate position.

Examples of adhering the side portions of the back face sheet to each other by heat sealing include a method of constituting an inter-labial pad by using a material capable of being heat sealed and utilizing the frictional heat caused by cutting a product. That is, when an absorbent body covered with a cover sheet is passed between a roll with a cutter blade and a flat roll and cut into the shape of a product, the material constituting the inter-labial pad is softened and melted and sealed by the heat of friction generated between the cutter blade and the flat roll. The materials melted and sealed by the frictional heat include, for example, a surface side sheet or back face sheet impregnated with a thermoplastic resins or adhesives. The heat sealing material may be provided only at the backward end, or the heat sealing material may be used in a larger amount in the backward end than that in other regions. Further, a material with a softening point lower than that of other regions may also be disposed to the backward end.

Other means for adhering at least the side portions of the back face sheet releasably to each other without using the adhesive coating include a method of adhering the side portions of the back face sheet to each other by fir-engagement of materials constituting the inter-labial pad to each other so as to be released when necessary. Referring to a case of covering the absorbent body with a surface side sheet and a back face sheet as an example, when an inter-labial pad comprising a surface side sheet, an absorbent body and a back face sheet is folded in two along the longitudinal center line and then the backward end is passed between a convex emboss roll and a concave emboss roll, opposed surface side sheet and back face sheet engage to each other. Further, before folding the inter-labial pad, the surface side sheet and the back face sheet may be embossed respectively and then the inter-labial pad is folded in two thereby engaging the surface side sheet and the back face sheet to each other. The convex portion of the convex emboss roll has a height within a range of from 0.1 to 2 mm and a pitch within a range from 0.2 to 10 mm, while the concave portion of the concave emboss roll has such a shape as fit-engaging therewith.

(7) The inter-labial pad as described in any one of (1) to (6) wherein the width of the backward end is narrower than the width of the forward end.

According to this embodiment of the present invention, since the width of the forward end at the top portion to be in contact with the forward of the labia is larger than that of the backward end, the inter-labial pad can be more reliably retained in the labia.

Herein, the inter-labial pad is kept to be held between the labia without falling off by the competition of the inter-labial pressure exerting on the inter-labial pad with the compression repulsive force from the inter-labial pad caused by being compressed by the inter-labial pressure. Further, since the labium minus pudenda has a shape in which the forward is thicker and longer compared with the backward, the force of the forward inter-labial pressure is higher. Then, in the inter-labial pad according to (7), since the width at the forward end is larger than the width at the backward end, the compression repulsive force at the forward end is elevated so as to make the inter-labial pad hardly to fall off.

(8) The inter-labial as described in (7), wherein the width for the top portion at the backward end is from 0.5 mm to 5 mm, and the width for the top portion at the forward end is from 3 mm to 15 mm.

According to this embodiment of the invention, the width of the backward end is within a range from 0.5 to 5 mm, and the width for the forward end is from 3 to 15 mm. In a case when the width for the top portion is within the range described above, it is possible to prevent foreign-body sensation given to a wearer and increase the compression repulsive force of the inter-labial pad. The width for the backward end is particularly preferably within a range from 1 to 3 mm, and the width for the forward end is particularly preferably from 4 to 10 mm. Further, while the width for the forward end and the width for the backward end may be changed discontinuously, it is preferred to constitute the top portion such that the width is continuously changed gradually since gaps are hardly generated between the pad and the labial inner wall.

According to this embodiment of the present invention, the inter-labial pad can be inserted easily and reliably while preventing deformation of the inter-labial pad or injuries given to the inside of the labia.

DESCRIPTION OF THE SYMBOLS

| | |
|---|---|
| 1, 2, 3 | inter-labial pad |
| 10, 20, 30 | top portion |
| 10a, 20a, 30a | forward end |
| 10b, 20b, 30b | backward end |
| 11, 12, 21, 22, 31, 32 | side portion |
| 15, 25, 35 | surface side sheet |
| 16, 26, 36 | back face sheet |
| 17, 27, 37 | absorbent body |

DESCRIPTION OF THE PREFERRED EMBODIMENTS

Preferred embodiments of the present invention will be explained with reference to the drawings. In the following descriptions, identical members are labeled with identical numerals or symbols for which description is omitted or simplified.

First Embodiment

Figure 1:
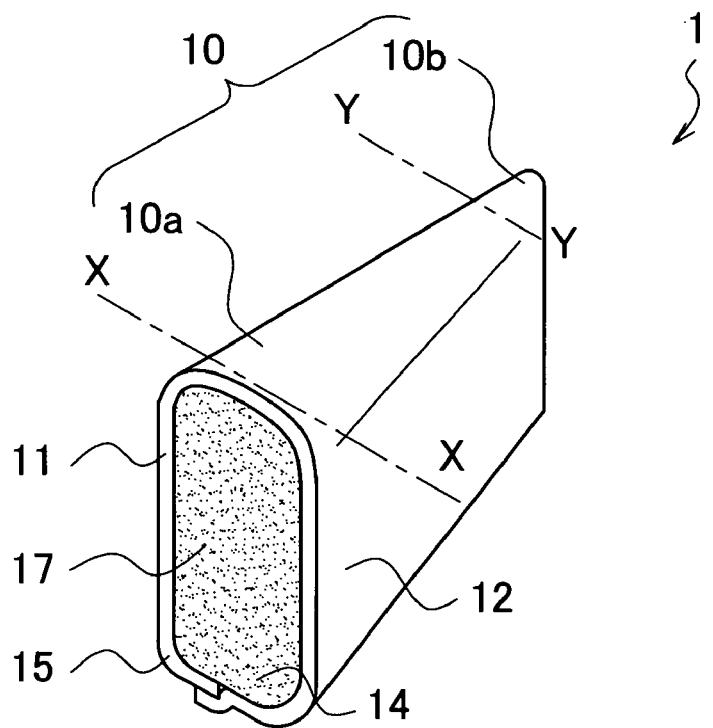
FIG. 1 is a perspective view of an inter-labial pad according to a first embodiment of the prevent invention.
Figure 2:
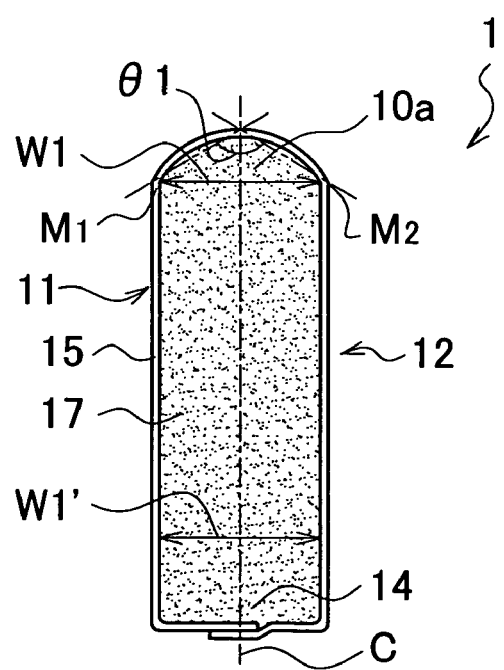
FIG. 2 is a cross sectional view taken along line X-X of the inter-labial pad according to the embodiment described above.
Figure 3:
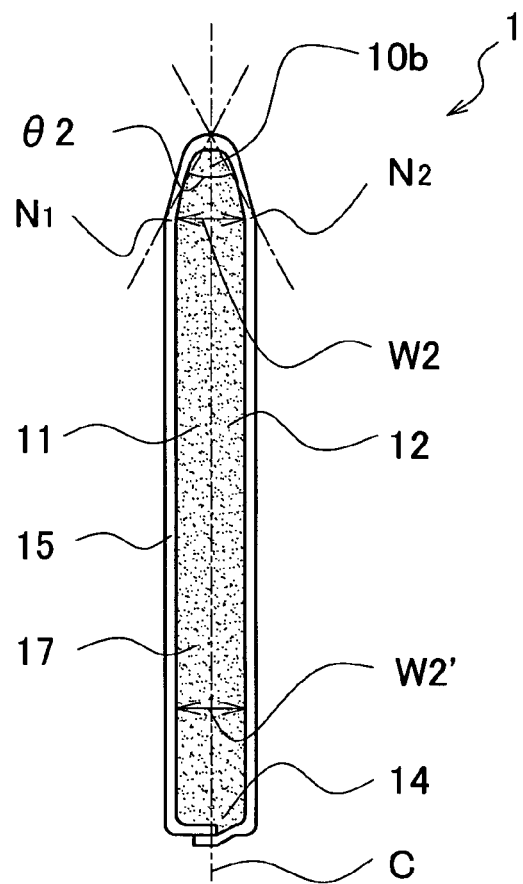
FIG. 3 is a cross sectional view taken along line Y-Y of the inter-labial pad according to the embodiment.

FIG. 1 is an entire perspective view of an inter-labial pad 1 according to a first embodiment of the present invention. In the inter-labial pad 1, when the inter-labial pad is attached to wearer's labia, a portion in contact with a forward portion of labia is referred to as a forward portion, while a portion in contact with the backward portion of labia is referred to as a backward portion. FIG. 1 shows a situation where the inter-labial pad 1 is viewed from the forward side. FIG. 2 is a cross sectional view along line X-X and FIG. 3 is a cross sectional view along line Y-Y of the inter-labial pad 1.

The inter-labial pad 1 is substantially in a pillow-like shape comprising an absorbent body 17, and a surface side sheet 15 as a cover sheet in which a substantially semi-cylindrical top portion 10 extends in the longitudinal direction. Lateral side portions 11 and 12 are provided on both sides of the top portion 10. The inter-labial pad 1 is inserted between the labia such that the top portion 10 is in contact with the oitium vaginae in the inner part of the labia and the lateral side portions 11, 12 are in contact with a pair of opposing labia inner walls respectively. In the inserted state, a portion vertically extending downward from the top portion 10 forms a bottom portion 14 and the bottom portion 14 may protrude out of the labia.

The top portion 10 has a forward end 10a situating on the forward side and a backward end 10b situating on the backward side in which the backward end 10b has a width narrower than that of the forward end 10a and has a sharp shape. That is, the width W2 for the backward end 10b shown in FIG. 3 is narrower than the width W1 for the forward end 10a shown in FIG. 2. Further, the angle of the top portion 10 is also gradually narrowed from the forward end 10a to the backward end 10b. That is, the angle θ1 for the backward end 10b is smaller than the angle θ1 for the forward end 10a. That is, the "sharp shape" specifically means that the width W2 for the backward end 10b is within a range from 0.5 to 5 mm, preferably, within a range from 1 to 3 mm. Further, it is preferred that the angle θ2 for the backward end 10b is within a range from 2 to 45°, particularly, from 3 to 20°.

On the other hand, the width W1 for the forward end 10a is, preferably, within a range from 3.0 to 15.0 mm and, particularly, within a range from 4.0 to 10.0 mm. The angle θ1 is, preferably, within a range from 30 to 1500, and, particularly, from 40 to 800. While the angle for the top portion 10 may be changed stepwise, that is, discontinuously from the forward end 10a to the backward end 10b, a gradual difference provided as in the inter-labial pad 1 shown in FIG. 1 is preferred since a gap is less graduated between the labial inner wall and the inter-labial pad 1.

Herein, the method of measuring the width and the angle for the top portion 10 will be explained. The width for the top portion 10 means, as shown in FIGS. 2 and 3, a length of a line (virtual horizontal line) connecting two points at which lateral side portions 11 and 12 extending vertically in the inserted state are in contact with the top portion 10 and, specifically, the distance between points $M_1$ and point $M_2$ is the width W1 for the forward end 10a. In the same manner, the length of a line connecting the point $N_1$ and the point $N_2$ is the width W2 for the backward end 10b.

The angle for the top portion 10 is an angle of intersection between two lines drawn from the point where a line (center axis C) extending passing through the lateral center of the top portion 10 and in parallel with the lateral side portions 11 and 12 intersects the top portion 10 to the points where the top 10 and the lateral side portions 11 and 12 are in contact with each other (two points $M_1$, $M_2$ in FIG. 2), which correspond to θ1 in FIGS. 2 and θ2 in FIG. 3. In a case of measuring the width and the angle, a sample is measured in a free state substantially under no-load when the inter-labial pad is taken out of a packaging container.

Further, the dimensional ratio of the width between the top portion 10 and the bottom portion 14, that is, the dimensional ratio between the width W1 for the top portion 10 and the width W1' for the bottom portion 14 on the forward side is not particularly restricted. However, it is preferred that the width is narrowed from the top portion 10 toward the bottom portion 14. Specifically, the width W1' for the bottom portion 14 in the forward side is preferably equal with or less than the width W1 for the top portion 10. This is because the labium majus pudenda situate to the outside of the labium minus pudendi near the vestibular floor in the labia, and the inter-labial pressure increases from the front of the labium minus pudendi to the vestibular floor, and, accordingly, the inter-labial pad 1 can be made less to fall off by changing the compression repulsive force conforming to the gradient of the inter-labial pressure. This is also applicable for the width W2 and width W2' in the backward side.

The forward end 10a of the top portion 10 means a region of the top portion 10 inserted between the labia, that is, the forward portion of a region of the inter-labial pad, where the inter-labial pad 1 is in contact with the depth of the labia, while the width and the angle of the other region of the inter-labial pad 1 where the inter-labial pad 1 is exposed from the labia are not limited. Specifically, the width for the top portion 10 exposed from the inter-labia space may be in a range for W1 or W1', or may be in a range for W2 or W2', and the angle may be in a range for θ1 or in a range for θ2. It is, however, preferred for the inter-labial pad 1 as described above to constitute such that the width for the forward end 10a of the top portion 10 is the largest and the width is narrowed toward the backward (that is, to the backward end 10b) and to the bottom portion 14 so as to reduce the compression repulsive force.

Second Embodiment

Then, an inter-labial pad 2 according to a second embodiment of the present invention will be described with reference to FIGS. 4 to 11. An inter-labial pad 2 comprises an absorbent body 27 substantially of a plate-like shape in the plan view, a surface side sheet 25 and a back face sheet 26 covering the absorbent body 27. In this embodiment, the cover sheet comprises a liquid permeable surface side sheet 25 and a less liquid permeable back face sheet 26.

Figure 4:
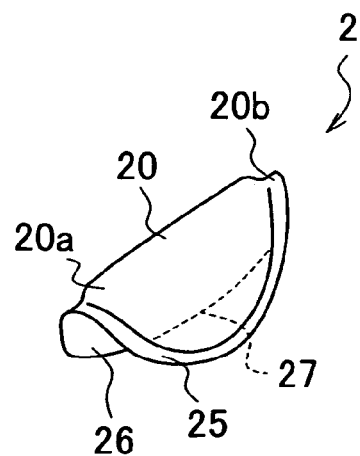
FIG. 4 is a perspective view of an inter-labial pad according to a second embodiment of the invention.

FIG. 4 is an entire perspective view for the inter-labial pad 2 as viewed from the forward side in which the inter-labial pad 2 is folded in two along the longitudinal center line such that the opposed side portions of the back face sheet 26 come in contact with each other and a top portion 20 extending from the forward to the backward of the inter-labial pad 2 is formed along the fold. Both sides of the top portion 20 are lateral side portions 21, 22 in contact with the labial inner walls in the inserted state of the inter-labial pad 2. In this embodiment, the side portions of the back face sheet 26 opposed at the backward of the inter-labial pad 2 are adhered releasably to each other to form a backward end 20b of a sharp shape.

Figure 5:
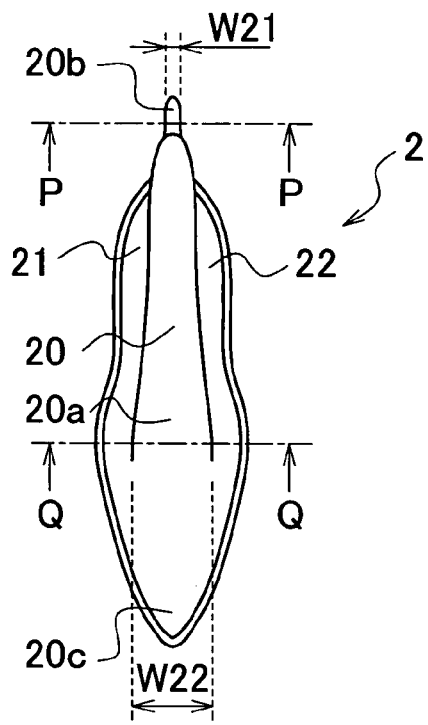
FIG. 5 is a plan view of the inter-labial pad according to the embodiment described above.
Figure 6:
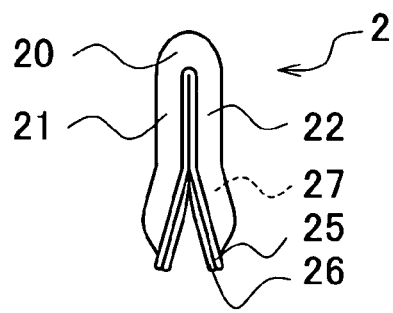
FIG. 6 is a rear view of the inter-labial pad according to the embodiment described above.

FIG. 5 is a plan view of the inter-labial pad 2 as viewed from the side of the top portion 20 and FIG. 6 is a back view as viewed from the back side. As shown in FIG. 5, the width of the top portion 20 increases from the backward toward the forward of the inter-labial pad 2, and the portion situated on the side substantially opposite to the backward end 20b forms a forward end 20a in contact with the forward of the labia. The region ahead of the forward end 20a forms an exposed portion 20c protruding out of the labia when the inter-labial pad 2 is inserted.

Figure 7:
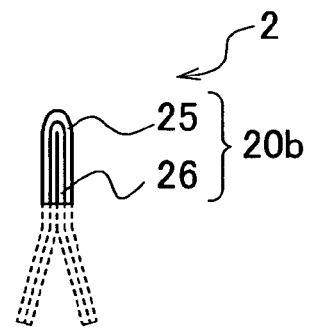
FIG. 7 is a cross sectional view for a backward end of the inter-labial pad according to the embodiment described above.
Figure 8:
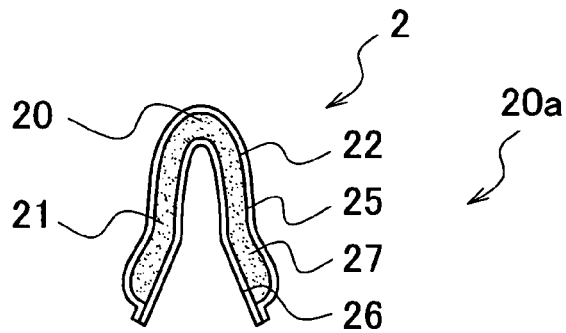
FIG. 8 is a cross sectional view for a forward end of the inter-labial pad according to the embodiment described above.

FIG. 7 is a cross sectional view for the backward end 20b of the top portion 20 as viewed in the lateral direction, that is, along arrow P-P. FIG. 8 is a cross sectional view for the forward end 20a as viewed in the lateral direction, that is, along arrow Q-Q. As shown in FIG. 7, the backward end 20b comprises merely a surface side sheet 25 and a back face sheet 26, that is, an absorbent body 27 is not enclosed between the surface side sheet 25 and the back face sheet 26, and the side portions of the back face sheet 26 are adhered to each other to form a sharp shape with a narrow width and of small angle. On the other hand, as shown in FIG. 8, the other side portions of the back face sheet 26 are not adhered at the forward end 20a.

In FIG. 6, for the portion where the surface side sheet 25 and the back face sheet 26 are in contact, three parallel lines are shown along the vertical direction in the drawing, while five parallel lines are shown in the vertical direction of the drawing in FIG. 7. This is because the adhesives coated between the surface side sheet 25 and the back face sheet 26 of the inter-labial pad 2 are exuded between both of the sheets upon cutting to adhere also the side portions of the surface side sheet 25 with each other. That is, in FIG. 7 as a cross sectional view for the backward end 20b, while FIG.

7 shows a cross section in which the surface side sheet 25 and the back face sheet 26 are laminated, whereas FIG. 6 shows a case in which the inter-labial 2 covered with the surface side sheet 25 folded at the end face of the backward end 20b as viewed at the back. As in the inter-labial pad 2, since the end face of the backward end 20b is covered with the surface side sheet 25, adhesives interposed between the surface side sheet 25 and the back face sheet 25 and exuded upon cutting can be prevented from being in direct contact with a wearer's body.

Figure 9:
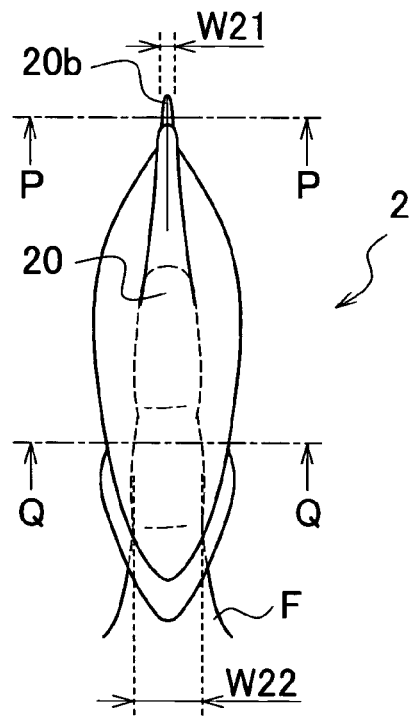
FIG. 9 is a view showing a state in which a finger is put on the inter-labial pad according to the embodiment described above.
Figure 10:
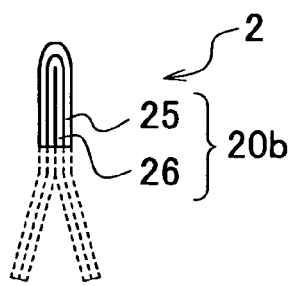
FIG. 10 is a cross sectional view for a backward end of the inter-labial pad shown in FIG. 9.
Figure 11:
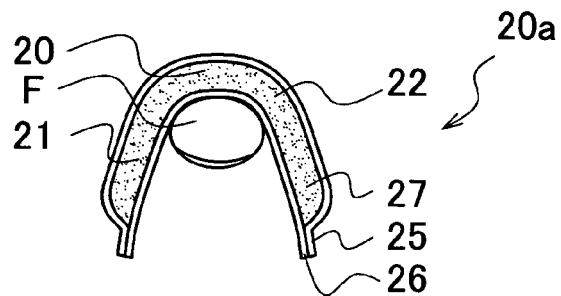
FIG. 11 is a cross sectional view for a forward end of the inter-labial pad shown in FIG. 9.

FIG. 9 shows a state where a finger F is put along the back face sheet 26 of the inter-labial pad 2. FIG. 10 is a cross sectional view taken along arrow P-P for the backward end 20b of the inter-labial pad 2 in the state shown in FIG. 9, and FIG. 11 is a cross sectional view taken along arrow Q-Q for the forward end 20a. As shown in FIGS. 7 to 11, when the finger F is put along the back face sheet 26, while the shape of the forward end 20a changes, the backward end 20b maintains a sharp shape. The method of using the inter-labial pad 2 will be described specifically later.

Third Embodiment

Figure 12:
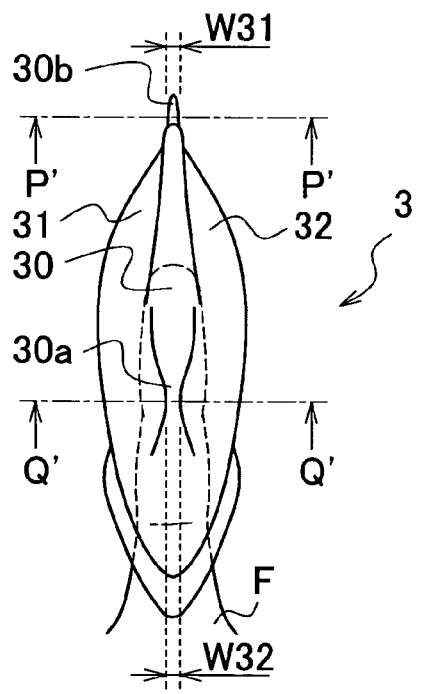
FIG. 12 is a plan view in a state in which a finger is put on an inter-labial pad according to a third embodiment of the invention.

Further, an inter-labial pad 3 of a third embodiment which is a modified embodiment of the inter-labial pad 2 of the second embodiment will be explained. FIG. 12 is a plan view in a state of putting a finger F to the side of a back face sheet 36 of an inter-labial pad 3, as viewed on the side of a top portion 30. The inter-labial pad 3 has an identical constitution with that of the inter-labial pad 2 excepting that adhesives are coated to side portions of the back face sheet 36 on the forward and side portions of the back face sheet 36 on the forward are adhered to each other.

Since the side portions of the back face sheet 36 on the forward are adhered to each other, the width W32 and the angle for the forward end 30a of the top portion 30 scarcely change even when the finger is put on the inter-labial pad 3. Thus, even in a case where the forward of the labia is not easy to open, the inter-labial pad 3 can intrude easily also to the forward of the labia, and the forward of the inter-labial pad 3 can also be attached in appropriate position. More specifically, it is most preferred that the width 32 is within a range from 4.0 to 8.0 mm and the angle is within a range from 30 to 80° for the forward end 30a irrespective that the finger is put or not.

Means for rendering the width W32 and the angle for the forward end 30a less fluctuating is not restricted to the adhesion of the side portions of the back face sheet 36 to each other. However, when the side portions of the back face sheets 36 are adhered to each other as in this embodiment, the side portions of the back face sheet 36 can be adhered to each other by heat sealing such as by embossing, etc. A portion where the portions of the back face sheet 36 are adhered to each other is within 15 mm, preferably, within 10 mm from the top end of the top portion 30 to the lateral sides 31, 32 of the inter-labial pad 3. If the size exceeds the range, since it becomes harder to detect the vestibular floor by the finger, it is difficult to attach the inter-labial pad in appropriate position.

In a case where the side portions of the back face sheet are adhered to each other as in examples shown in the second embodiment and the third embodiment, the adhered side portions of the back face sheet are preferably adhered such that they are releasable by the pressure of attachment. Means for releasably adhering the side portions of the back face sheet to each other includes coating of adhesives, heat sealing and engaging embossing, etc.

Further, a mini-sheet piece may be provided to the back face sheet of the inter-labial pad having a substantially plate-like shape and used in a state folded in two as shown in the second embodiment and the third embodiment. The mini-sheet piece preferably covers a portion of the back face sheet and is adhered to the back face sheet at the peripheral edge of the inter-labial pad. By providing such a mini-sheet piece, a finger insertion opening into which a finger is inserted is formed between the mini-sheet piece and the back face sheet, and the inter-labial pad can be retained more stably to the finger.

Further, the inter-labial pad according to the present invention may be contained individually in a wrapping container. By wrapping individual inter-labial pads into separate wrapping containers (individual wrapping container) respectively, the inter-labial pad can be carried about and stored in a sanitary manner.

<Method of Using Inter-Labial Pad>

Figure 15:
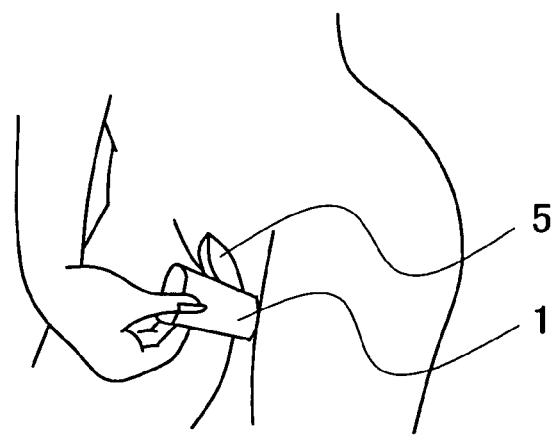
FIG. 15 is a view showing the state of attaching the inter-labial pad according to the first embodiment.
Figure 16:
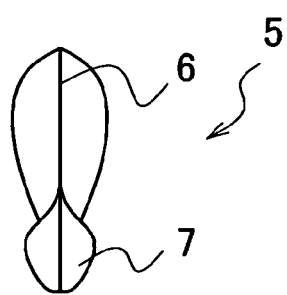
FIG. 16 is a front elevational view for labia with a portion of the backward being opened.
Figure 17:
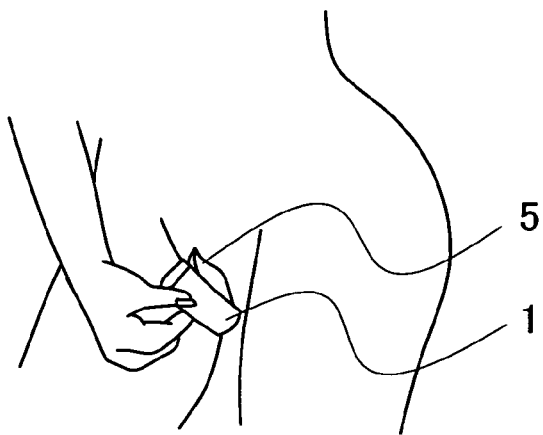
FIG. 17 is a view showing the state of attaching the inter-labial pad according to the first embodiment.
Figure 18:
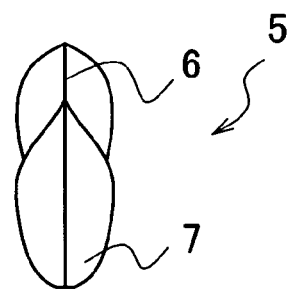
FIG. 18 is a front elevational view of labia opened from forward to backward portions.

Then, the method of using the inter-labial pad according to the present invention will be explained. FIG. 15 shows a state where the inter-labial pad 1 according to the first embodiment is started to be inserted into the labia 5. FIG. 16 is a front elevational view of the labia 5 opened at a portion of backward 7. FIG. 17 shows the next state of inserting the inter-labial pad 1 while opening between the labia 5. FIG. 18 is a front elevational view of the labia 5 in a state opened widely from the backward 7 to the forward 6. The inter-labial pad 1 is inserted between the labia 5 from backward 7 of the labia which is situated at the dorsal side, short and thin and easy to open, and held between the labia in a state where the lateral sides 11 and 12 are in contact with the labial inner wall by the inter-labial pressure and the compression repulsive force of the inter-labial pad.

By the way, while the depth of the labia extending vertically from the side of the thigh to the ostium vaginae in a standing state where a woman is standing up is individually different, it is about 14 mm as an average value. Accordingly, the inter-labial pad is attached to the labia in a region within 14 mm extending vertically from the thigh to the ostium vaginae in the standing up state. Further, in an inter-labial pad whose shape changes before and after the insertion between the labia, for example, an inter-labial pad of a substantially plate-like shape and inserted in a folded state, portions within 14 mm from the longitudinal center line to both lateral directions respectively are held between the labia.

Further, the average length of the labia extending from the forward to the backward is 55 mm, with 50 mm to the forward and 5 mm to the backward from the ostium vaginae. Accordingly, the inter-labial pad is put between the labia within 50 mm for the forward and within 5 mm for the backward from the position in contact with the ostium vaginae.

Accordingly, the total dimension for the outer profile of the inter-labial pad in the longitudinal direction is preferably from 40 to 180 mm and, more preferably, from 80 to 120 mm irrespective of the shape. Further, the total dimension in the lateral direction is, preferably, from 20 to 100 mm and, more preferably, from 50 to 80 mm. The total dimension in the lateral direction is a total dimension extending from the vestibular floor to the ostium vaginae in the vertical direction in a inserted state. In a case where the inter-labial pad is larger than the length or/and width of the labia, a portion of the inter-labial pad becomes exposed out of the labia, however, such exposed area (20c in FIG. 5) may be allowed.

The shape of the inter-labial pad is substantially pillow-like in the first embodiment and substantially elliptic shape folded in two in the second and the third embodiments but not limitative to them and any shape may be used so long as it conforms the female labia. Other shapes conforming to the female labia can include, an hourglass type, a droplet type, etc.

Then, an operation of inserting the inter-labial pad 2 according to the second embodiment will be explained. As shown in FIG. 9, a finger F is put along the longitudinal center axis of the back face sheet 26, and the inter-labial pad 2 is inserted from the backward end 20b of the top portion 20 to the backward of the labia. In the inter-labial pad 2, since the side portions of the back face sheet 26 are adhered to each other at the backward end 20b, as shown in FIG. 7 and FIG. 10, the width W21 for the backward end 20b does not fluctuate before and after the insertion of the finger F. Specifically, in FIG. 7 and FIG. 10, it is preferred that the width W21 for the backward end 20b is preferably within a range from 1.0 to 3.0 mm and the angle thereof is within a range from 3 to 20° irrespective that whether the finger F is put or not.

As described above, since the backward end 20b of the top portion 20 of the inter-labial pad 2 maintains a sharp shape even when the finger F is inserted, it can be inserted easily between the labia. After the backward end 20b has inserted to the backward of the labia, the wide forward end 20a of the inter-labial pad 2 is inserted at the forward of a labia while expanding the forward of the labia with fingers and then attached between the labia.

Figure 19:
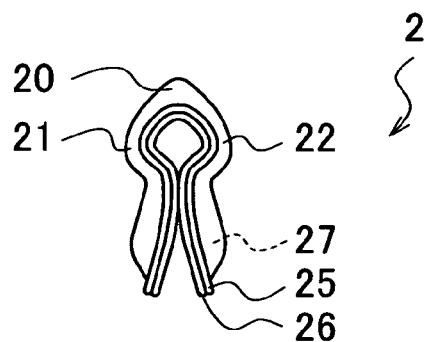
FIG. 19 is a view showing the inserted state of the inter-labial pad according to the second embodiment.

FIG. 19 shows an inter-labial pad 2 in an inserted state where it is attached between the labia and deformed. The inter-labial pad 2 inserted between the labia is in contact at lateral sides 21, 22 with the inter-labial inner walls, and at the top portion 20 with the ostium vaginae at the depth of labia (vestibular floor). The side portions of the back face sheet 20 situated at the forward end 20a of the inter-labial pad 2 are not adhered but releasable with each other and can be deformed by the wearing pressure generated by the change of the wearer's posture. Accordingly, the inter-labial pad 20 can deform in accordance with the wearer's movement so as to be in close contact with the labial inner walls to prevent the leakage of menstrual blood. Further, the side portions of the back face sheet 26 adhered to each other at the backward end 20b are released, after insertion of the inter-labial pad 2, by the wearing pressure generated in accordance with the wearer's movement and can follow-up the movement of the labia.

Figure 13:
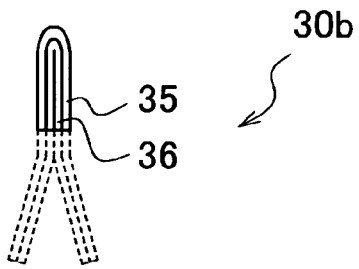
FIG. 13 is a cross sectional view for a backward end of the inter-labial pad shown in FIG. 12.
Figure 14:
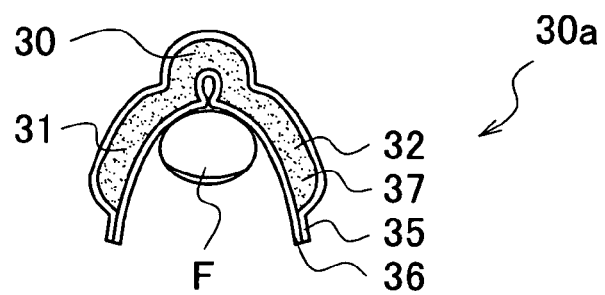
FIG. 14 is a cross sectional view for a forward end of the inter-labial pad shown in FIG. 12.

On the other hand, in the inter-labial pad 3 according to the third embodiment shown in FIGS. 12 to 14, the side portions of the back face sheet 36 at the forward end 30b are releasably adhered to each other. Accordingly, the width W 32 for the forward end 30a of the top portion 30 is always substantially constant whether the finger is put therealong or not. While the side portions of the back face sheet 36 situated at the forward end 30a of the inter-labial pad 3 are adhered, since the adhered portion at the forward end 30a is releasable by the wearing pressure by a wearer, the adhered side portions of the back face sheet 36 are released from each other and the inter-labial pad 3 can freely deform following-up the movement of the labia, after inserting the inter-labial pad 3. In the same manner, the adhered side portions of the back face sheet 36 at the backward end 30b are also releasable from each other, and the inter-labial pad 3 can deform such that it can follow-up the movement of the labia also at the backward end 30b.

<Constitutive Material for Inter-Labial Pad>

The constituent material for the inter-labial pad according to the invention will be explained.

[Absorbent Body]

For providing the absorbent body with compressibility not giving foreign-body sensation to a wearer, the material is preferably bulky and, preferably, less deformed and gives less chemical stimulations. Specifically, the absorbent body can comprise paper, single or composite synthetic fibers or other materials alone or in admixture. The material constituting the absorbent body includes, for example, natural pulp, chemical pulp, rayon, acetate, natural cotton, super absorbent polymer and foams. Among the materials described above, it is preferable to use physically embossed rayon or acetate, chemical pulp cross-linked and crimped by cross-linking agent or composite synthetic fibers as the main component in view of the bulkiness of the material. Composite synthetic fibers include those of core-sheath type, core-sheath eccentric type or side-by-side type fibers utilizing the heat shrinkage of resins such as polyethylene(PE), polypropylene(PP), or polyethylene terephthalate (PET), etc. Further, fibers with molecular orientation increased by being stretched at the stage of spinning or profiled fibers of unusual type such as having Y- or C-form cross sectional shape may also be mixed. Furthermore, an oil agent may be coated on or contained in fibers in order to enhance the slipping property between the fibers.

The materials described above may be sheeted by an air laid method, spun lacing method, papermaking method or melt blown method or the like, and formed into the absorbent body by needling or embossing fabrication thorough passage between rolls having an emboss pattern such as a dot-shape, lattice-shape or corrugated shape, etc to form an absorbent body. Further, the absorbent body may be applied with slitting for obtaining flexibility. Further, the embossed area ratio is within a range from 0.1 to 60% and, preferably, within a range from 1 to 30%.

As a specific examples of the absorbent body is the one in which 5 to 100% of core-sheath eccentric type synthetic fibers comprising PE and PP in admixture (fiber length: 51 mm, crimping ratio of fibers: 60%, deposited with 0.2% of hydrophilic oil agent, fiber denier: 4.4 dtex) and 95 to 0% of rayon (fiber length: 51 mm, crimping ratio of fibers: 50%, deposited with 0.2% of hydrophilic oil agent, fiber denier: 3.3 dtex) are mixed in these mixing ratios, fiber-opened collected and then applied be embossing with a dot-shape emboss pattern.

[Surface Side Sheet]

A surface side sheet is constituted with a material having liquid permeability for allowing a body fluid to permeate therethrough and a hydrophilicity and hardly giving stimulations to skins. Specifically, the surface side sheet can be constituted with a non-woven fabric constituted from synthetic fibers by a point-bonding method or air through method, etc., and used alone or in a composite form. Further, the surface side sheet may also be constituted with a film comprising a thermoplastic resin and having permeation apertures, or a composite film formed by laminating a film to a fiber layer and having permeation apertures, etc. The fibers constituting the non-woven fabric include those fibers from materials of thermoplastic resins such as PE, PP, and PET, alone or as a composite fiber form of core-sheath type, core-sheath eccentric type or side-by-side type film. In view of the hydrophilicity with the body fluid, the non-woven fabric may also be incorporated with cellulosic hydrophilic fibers such as natural pulp, chemical pulp, rayon, acetate and natural cotton in addition to the synthetic fibers described above.

Among the materials described above, spun lace non-woven fabrics formed from fibers obtained by mixing from 5 to 30% of rayon or acetate and from 70 to 95% of polyethylene terephthalate, adjusted within a range from 20 to 60 g/m$^2$ and then had the fibers entangled one another by hydroentanglement, dried, and adjusted to the thickness within a range from 0.3 to 1.0 mm are particularly preferred as the surface side sheet.

[Back Face Sheet]

As a back face sheet, those having less liquid permeability so as to be capable of preventing menstrual blood retained in the absorbent body from leaking to the outside of the inter-labial pad are used. Further, by constituting the back face sheet with a material having moisture permeability, it is possible to decrease steaming during wearing of the inter-labial pad and reduce uncomfortable feeling during wearing.

The less liquid permeable sheets include those materials made of films comprising PE, PP, PET, polyvinyl alcohol, polylactic acid or polybutyl succinate, non-woven fabrics papers and materials obtained by laminating them at a thickness from 15 to 60 μm. Further, the sheet may also be an air permeable film obtained by filling resin with an inorganic filler in the resin and applying a stretching treatment thereto. Specifically, the sheets include those films mainly comprising a low density polyethylene resin and adjusted to a basis weight per unit area within a range from 15 to 30 g/m$^2$, or air permeable films adjusted to an aperture area ratio within a range from 10 to 30% and an aperture diameter within a range from 01 to 0.6 mm. Examples of the non-woven fabrics include spun bonded non-woven fabrics, point-bonded non-woven fabrics, air through non-woven fabrics, etc., which may be applied with a water repelling treatment. Among them, an SMS (spun bonded layer/melt blown layer/spun bonded layer) non-woven fabrics containing melt blown fibers, constituted with ultrafine fibers and having extremely small inter-fiber distance are preferred. In this case, the basis weight per unit are is, preferably, within a range from 5 to 15 g/m$^2$ for spun bonded layer, from 1 to 10 g/m$^2$ for melt blown layer, from 5 to 15 g/m$^2$ for spun bonded layer respectively.

[Mini-Sheet Piece]

The mini-sheet pieces may be similar to those explained for the surface side sheet and the back face sheet. Further, laminates of fibers with elastic (elastic fibers), films and foamed materials having air cells may be utilized. Elastic fibers are those fibers constituted with thermoplastic resins such as PE, PP and PET, each of the resins being used alone or as a composite to form core-sheath type, core-sheath eccentric type or side-by-side type fibers, and fibers obtained from the fibers described above having been applied secondary crimping by mechanical crimping or heating, etc. have elasticity and are preferred. In view of the feeling of wearing due to elasticity and rigidity, those selected from the fiber length of from 3 to 64 mm with a fiber denier from 0.5 to 8.8 dtex and adjusted to a thickness within a range from 0.2 to 3.0 mm, preferably, within a range from 0.5 to 1.5 mm are utilized preferably.

Elastic fiber laminates can include, for example, non-woven fabrics using elastic fibers, and the methods of manufacturing the non-woven fabrics using the elastic fibers include, an air through method, point bonding method, spun bonding method, spun lacing method, etc. Particularly, non-woven fabrics formed by the air through method by lami- nating fibers in a card and bonding them by melt-bonding the thermoplastic fibers are preferably used because it has repulsive elasticity. Naturally, non-woven fabrics utilized manufactured by generally used methods such as the point bonding method, spun bonding method or spun lacing method can also be utilized. Further, spun bonded non-woven fabrics formed by spinning continuous filaments and bonding them by heat-embossing can also be utilized and the SMS non-woven fabrics formed by blow-bonding melt-blowing fibers to the spun-bonded fibers can also be utilized. A chemical bonding method or an air laid method of coating a binder to the surface after the fiber lamination is also utilized as the manufacturing method for the non-woven fabrics. Further, those sheets formed by using the materials described above alone or multi-layering them fixed by adhesives or embossing may also be utilized. Further, those sheets adjusted for the repulsive resiliency and thickness by way of the emboss pattern may also be utilized preferably.

Further, the films include those of resins such as elastic PE, PP or PET, or highly elastic urethane or rubber and extruded through T-die or inflation molding alone, in a composite form, or in a multi-layered structure.

The foamed materials include those obtained by foaming resins such as elastic PE or PP, or highly elastic urethane or rubber. Furthermore, cellulose sponge having absorbability can also be utilized. The foamed product may be either an open cell type or a closed cell type.

[Individual Packaging Container]

Materials for individual packaging containers include films of PE, PP, PET, polyvinyl alcohol, polylactic acid or polybutyl succinate, non-woven fabrics, paper and laminated materials thereof at a thickness of 15 to 60 μm. Further, they include films applied with stretching for increasing the resin orientation. Examples of the non-woven fabrics include spun bonded non-woven fabrics, point-bonded non-woven fabrics, air through non-woven fabrics, etc., which may be applied with a water repelling treatment. When SMS non-woven fabrics is to be used, the basis weight per unit area is preferably within a range from 5 to 15 g/m$^2$ for spun bonded layer, from 1 to 10 g/m$^2$ for melt blown layer, from 5 to 15 g/m$^2$ for spun bonded layer respectively. Specifically, they include films formed by mixing from 0 to 80% of a low density polyethylene resin and from 100 to 20% of a high density polyethylene and adjusting to the basis weight per unit area within a range from 15 to 35 g/m$^2$.

Further, it is preferred that the individual packaging container can shield the color of menstrual blood absorbed by the inter-labial pad and a pigment is mixed within a range from 0.2 to 10%, or ink, etc. may also be printed. The inter-labial pads and the individual packaging containers may comprise water dispersability materials or biodegradable materials so that they can be flashed away.

<Manufacturing Method of Inter-Labial Pad>

Figure 20:
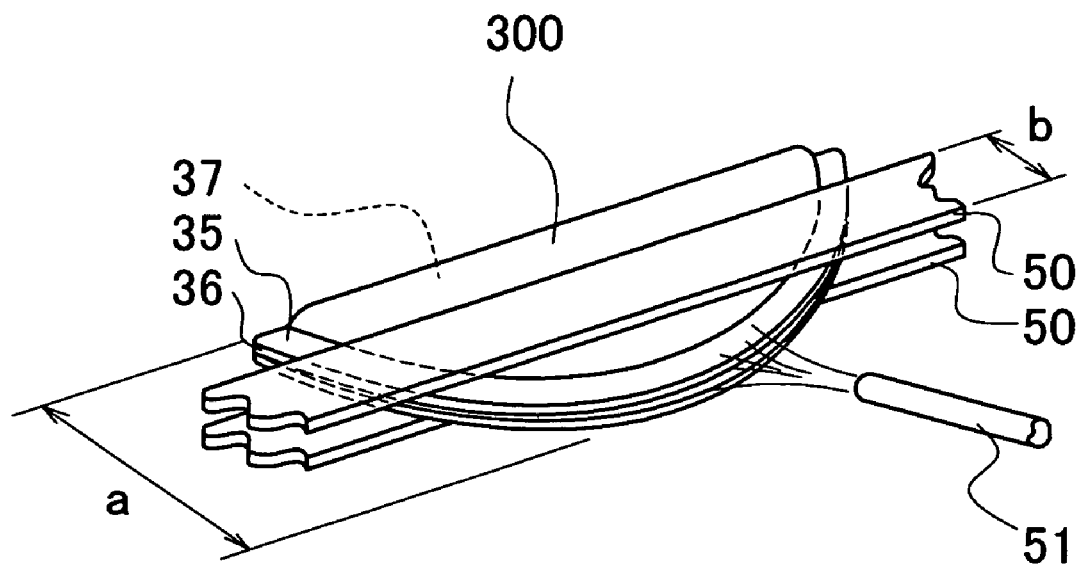
FIG. 20 is a schematic view showing a manufacturing step of the inter-labial pad according to the third embodiment.
Figure 21:
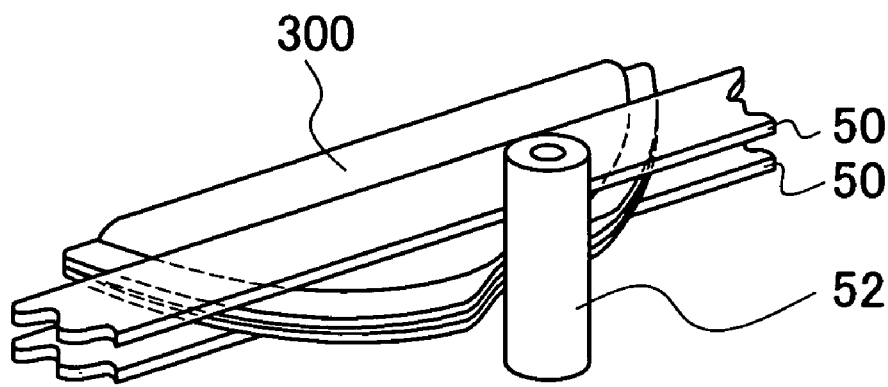
FIG. 21 is a schematic view showing a manufacturing step of the inter-labial pad according to the third embodiment.

Then, a manufacturing method of an inter-labial pad will be described for an example of the inter-labial pad 3 according to the third embodiment of the invention with reference to FIG. 20 and FIG. 21. FIG. 20 and FIG. 21 are schematic views showing a manufacturing step of the inter-labial pad 3.

The outline for the manufacture of the inter-labial pad 3 is as described below. As shown in FIG. 20, a laminate (not illustrated) in which an absorbent body 37 is interposed between the surface side sheet 35 and the back face sheet 36 is conveyed while being folded in two such that the side portions of the back face sheet 36 are opposed to each other, and the laminate is cut along a cutter shape larger than the absorbent body 37, to obtain a cutting product 300. The cut portion of the cutting product 300 is adhered by adhesives exuded between the surface side sheet 35 and the back face sheet 36, and the side portions of the back face sheet 36 folded in two and opposed to each other constitute a releasable adhered portion adhered releasably. Then, the side portions of the back face sheet 36 are released at a part of the adhered portion to partially open the joined portion, to obtain a inter-labial pad 3 in which the side portions of the back face sheet 36 situated at the forward end 30*a* and the backward end 30*b* are adhered releasably to each other.

A method of opening the part of the adhered portion will be described. After cutting the laminate at a position spaced apart by a predetermined space from the side edge of the absorbent body 37, the cutting product 300 thus obtained is conveyed while being put between two band-like conveyor belts 50. A pair of the conveyer belts 50 are opposed to each other at a predetermined distance such that they can sandwich the cutting product 300 between them. A pressurized air is blown from a nozzle 51 to a portion of the cutting product 300 conveyed being put between the conveyer belts 50, and the side portions of the back face sheet 36 at a portion of the cutting product 300 are released from each other by an air blowing pressure.

For applying the air blowing pressure efficiently to the cutting product 300, the nozzle 51 is preferably provided at a position where air is blown parallel with the adhered portion and to the center of the adhered portion. Further, the distance from the tip of the nozzle 51 to the adhered portion is preferably within a range from 1 to 100 mm and, particularly preferably, within a range from 5 to 30 mm. In a case where it is less than 1 mm, the cutting product may possibly collide against the nozzle when it meanders in the course of transportation likely to further exaggerate meandering. In a case where it is more than 100 mm, the air blowing pressure cannot be applied efficiently to the adhered portion.

The blowing pressure of air delivered from the nozzle 51 is, preferably, within a range from 0.01 to 5.00 MPa and, more preferably, within a range from 0.1 to 1.00 MPa. In a case where it is less than 0.01 MPa, the force of releasing the side portions of the back face sheet 36 from each other becomes weak and the adhered portion cannot be opened sufficiently. In a case where it is more than 5.00 MPa, the cutting product 300 meanders in the course of transportation.

It is preferred that the adhered portion of the cutting product 300 is exposed from the conveyer belt 50 since the blowing pressure of air is applied to the exposed portion more easily. Specifically, it is preferred that the width "a" of the cutting product 300 folded in two is larger than the width "b" of the conveyer belt 50 and it is sandwiched at the portion where the adhered portion is exposed. In this case, the width for the portion exposed from the conveyer belt is a-b (mm). Further, in this example, since the portion where the top portion 30 is formed is not held between the conveyer belts 50, application of an excessive fold can be prevented thereby preventing intense folding which would increase the rigidity of the top portion 30.

As described above, by blowing air to the portion where the side portions of the back face sheet 36 are adhered to each other to release the adhesion, it is possible to prevent the constituent member for constituting the inter-labial pad 3 from entangling to each other. That is, when the cutter blades for cutting the laminate are used continuously, they suffer from edge nicking to sometimes bring about a problem that fibers are entangled to each other at a cut face and the fibers of the mini-sheet piece entangle with the fibers of the back face sheet 36 making it difficult for the opening for the insertion of a finger, or a problem that fibers of the surface side sheet 35 entangle to each other to cause fluffing. Then, by blowing pressurized air as described above, such problems can be prevented to obtain an inter-labial pad 3 capable of preventing entanglement of fibers and easy to be attached, as well as also excellent in the feeling of wearing.

Further, it may be also arranged such that the cutting product 300 in which the side portions of the back face sheet 36 are adhered to each other is deformed by bringing it into contact with a resistive body and the side portions of the back face sheet 36 are released from each other by the impact upon the contact. FIG. 21 shows an example of bringing the cutting product 300 into contact with a resistive body to release the side portions of the back face sheet 36 from each other. The cutting product 300 conveyed being held between the conveyer belts 50 is in contact at a portion protruding out of the conveyer belts 50 with a cylindrical resistive body 52. The portion of the cutting product 300 in contact with the resistive body 52 is urged on the side of the conveyor belt 50 and thereby deformed in a direction vertical to the extending direction of the back face sheet 36 (vertical direction in FIG. 21) and released. The resistive body 52 is not particularly limited so long as it can open the joined portion and give such an impact as not causing meandering to the cutting product 300. Specifically, a cylindrical bar or a rotatable cylindrical roll can be mentioned.

The inter-labial pad 3 in which the side portions of the back face sheet 36 are adhered releasably to each other at the forward end 30*a* and the backward end 30*b* can be inserted easily into the labia, as well as can be conveyed stably in the manufacturing step of conveying the pad in a folded state as described above.

What is claimed is:

1. An inter-labial pad comprising an absorbent body that absorbs a body fluid, a surface side sheet covering one surface of the absorbent body being in contact with the labia in an inserted state, a back face sheet covering an opposite surface of the absorbent body, a top portion formed by folding the inter-labial pad along a longitudinal centerline of the inter-labial pad, such that the resulting two folded halves of the back face sheet oppose each other, the top portion being in contact with the labia in the inserted state;

a side edge portion formed by laminating the surface side sheet and the back face side sheet that cover the absorbent body;

a backward end of the top portion including paired side portions of the back face sheet formed by folding the inter-labial pad along the longitudinal center line, wherein the side portions at the top of the backward end are adhered and formed into a sharp shape for insertion between the labia; and a forward end of the folded side portions not adhered to each other and releasable along the longitudinal centerline, wherein the width of the forward end of the side edge portion is wider than the width of the backward end of the top portion.

2. The inter-labial pad according to claim 1; wherein the angle at the backward end of the top portion is smaller than the angle at the forward end of the top portion.

3. The inter-labial pad according to claim 2; wherein the angle at the backward end of the top portion is from 2° to 45°, and the angle at the forward end of the top portion is from 30° to 150°.

4. The inter-labial pad according to claim 1; wherein the inter-labial pad comprises a substantially flat absorbent body.

5. The inter-labial pad according to claim 1; wherein the two folded halves of the back face sheet are adhered to each other so as to be releasable by a pressure caused by a movement of a wearer.

6. The inter-labial pad according to claim 5; wherein the two folded halves of the back face sheet are adhered by application of heat sealing or engaging fabrication so as to be released when necessary.

7. The inter-labial pad according to claim 1; wherein the width of the backward end is narrower than the width of the forward end.

8. The inter-labial according to claim 7; wherein the width for the top portion at the backward end is from 0.5 mm to 5 mm, and the width for the top portion at the forward end is from 3 mm to 15 mm.

9. The inter-labial pad according to claim 1; further comprising a region ahead of the forward end of the top portion, forming an exposed portion protruding out of the labia when the inter-labial pad is inserted.

10. The inter-labial pad according to claim 5; wherein the two folded halves of the back face sheet are adhered by an adhesive.

11. The inter-labial pad according to claim 10; wherein a basis weight per unit area of the adhesive is within a range from 3 to 10 g/m$^2$.

* * * * *